United States Patent [19]

Mehnert

[11] 4,166,829

[45] Sep. 4, 1979

[54] LINEAR DIENE POLYMER HAVING REACTIVE TERMINAL GROUPS AND METHOD OF PREPARING THE SAME

[76] Inventor: Wolfgang Mehnert, Blumenstr. 13, Gundelfingen, Fed. Rep. of Germany, D-7803

[21] Appl. No.: 838,711

[22] Filed: Oct. 3, 1977

[30] Foreign Application Priority Data

Oct. 9, 1976 [DE] Fed. Rep. of Germany ....... 2645650

[51] Int. Cl.² ............................................. C07C 47/26
[52] U.S. Cl. ................................ 260/602; 260/601 H
[58] Field of Search ................ 260/602, 601 R, 601 H

[56] References Cited

U.S. PATENT DOCUMENTS 3,919,324  11/1975  Himmele et al. .................... 260/602

FOREIGN PATENT DOCUMENTS 1964962  7/1971  Fed. Rep. of Germany .......... 260/602

OTHER PUBLICATIONS

Merger, et al., "Chem Abs." vol. 85, (1976) p. 144852g.

Primary Examiner—Werren B. Lone
Attorney, Agent, or Firm—Toren, McGeady and Stanger

[57] ABSTRACT

When 1,3-butadiene, isoprene, chloroprene, or 2,3-dimethylbutadiene are held under polymerization conditions in the presence of allyl alcohol and a catalyst system consisting of a chloride or nitrate of a transition metal and the allyl alcoholate of sodium or lithium, there are obtained linear polymers having a terminal methylol group and a terminal formyl group and capable of further reactions characteristic of the terminal groups and the double bonds in the repeating units of the polymer chain.

9 Claims, No Drawings

LINEAR DIENE POLYMER HAVING REACTIVE TERMINAL GROUPS AND METHOD OF PREPARING THE SAME

This invention relates to diene polymers, and particularly to diene polymers having reactive terminal groups and to a method of preparing the polymers.

It is known from U.S. Pat. No. 3,296,227 to polymerize 1,3-butadiene and isoprene in the presence of a rhodium nitrate catalyst in allyl alcohol as a diluent to produce polymers of the dienes in which the trans or cis isomers predominate. The allyl alcohol does not enter into the polymer structure.

It has now been found that the dienes mentioned above and analogs thereof are converted to compounds of the formula

OCH—(CH$_2$)$_2$—R$_n$—(CH$_2$)$_3$—OH when the polymerization mixture additionally contains, as a co-catalyst, an alkali metal alcoholate of allyl alcohol. In the formula, R is C$_4$H$_{6-m}$X$_m$ and has a straight chain of four carbon atoms; X is hydrogen, methyl, or chlorine; m is 1 or 2 when X is methyl or hydrogen, and 1 when X is chlorine; and n is a number between 1 and 60.

The terminal formyl and methylol groups of the polymers react in the expected manner and permit the preparation of compounds which combine the rubber-like properties of polymers of the butadiene family with those of other constituents attached by reaction with the formyl and/or methyl groups, as will be illustrated below. Because of the presence of formyl groups and double bonds, the polymers tend to absorb oxygen from the air and are preferably prepared and stored in an atmosphere of nitrogen or other gas inert to the diene and the reaction product.

The polymerization is slow at room temperature of approximately 20° C. so that a temperature of at least 30° C. is preferred. At temperatures above 70° C., the yield is reduced by side reactions. The pressure in the polymerization zone has no significant bearing on the outcome of the reaction, and ambient atmospheric pressure is adequate if loss of the diene by evaporation can be either tolerated or prevented. A cold trap communicating with the gas phase in the reaction zone for receiving gaseous diene, and with the liquid phase for return of liquefied diene may be employed, and may be unavoidable for continuous operation. A sealed reaction chamber is preferred for batch operation, and the distribution of the diene between the gaseous and liquid phases can be shifted to accelerate the reaction by maintaining the highest gas pressure that the chamber is capable of containing.

The amounts of the two components of the catalyst system affect the yield and the molecular weight of the product in a manner that will be described below in more detail. Generally, it is preferred that the metal salt amount to 0.8 to 10 millimole per mole of butadiene present in the reaction mixture, and that the alkali metal present in the form of an alcoholate amount to 5 to 50 millimoles on the same basis. For highest yields, the amounts of metal salt and alkali metal should be approximately equimolecular, a deviation of ±20% being normally permissible. The amount of allyl alcohol employed is not critical. It must be greater than the combined weight of all the other components of the mixture and sufficient to dissolve the diene at the reaction temperature.

In addition to rhodium nitrate known from the aforementioned patent, other rhodium salts, such as the chloride or sulfate may be employed also salts of the other transition metals of the platinum group and of the iron group. Bismuth salts are marginally effective as catalysts in cooperation with alkali metal alcoholates. The activation energy for the reaction increases with the molecular weight of the alkali metal employed so that the alcoholates of lithium and sodium are greatly preferred over potassium, the catalytic effects of the corresponding cesium and rubidium compounds being too small for practical use.

When n in the formula of the product is greater than one, the repeating units in the polymeric compound produced from butadiene are mostly of the formula

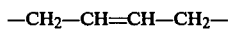

—CH$_2$—CH=CH—CH$_2$—

However, approximately 10% of the repeating units have been found to be of the formula

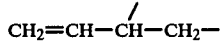

All repeating units are divalent and of the formula C$_4$H$_6$. The analogous two types of repeating units are found in approximately the same ratio in linear polymers of the invention produced from isoprene, 2,3-dimethyl-1,3-butadiene, and chloroprene and satisfy the formula C$_4$H$_{6-m}$X$_m$, as defined above.

The reaction medium should contain as little water and elementary oxygen as possible if yields close to 100% are to be achieved. Very small amounts of water may be introduced accidentally, particularly with the metal salts, and will affect the yield, probably by decomposing a corresponding amount of alcoholate. Whether a completely anhydrous reaction mixture in contact with a gaseous phase free from all traces of oxygen needs to be maintained must be determined under specific conditions as a matter of economics. The loss of product may be less costly than the purification of all components of the reaction mixture necessary to avoid such loss.

It is preferred to use allyl alcohol as the sole liquid solvent and diluent because of the convenience of recovery and simpler operation. However, other solvents inert to the starting materials and products may be present, such as benzene, toluene, petroleum ether, and ethanol.

The necessary reaction time varies with the temperature and other operating conditions, also with the yield that it is desired to achieve. A yield close to 100% can be achieved at the indicated preferred reaction temperatures with a sodium co-catalyst in 10 to 30 hours, with lithium in one to three hours.

The following examples are further illustrative of this invention.

EXAMPLE 1

In a glass pressure vessel, 85 mg sodium (3.7 mM) was dissolved in 65.3 g allyl alcohol (1.1 M) under a nitrogen blanket. When the sodium was dissolved, 1.008 g anhydrous rhodium nitrate (3.49 mM) was introduced with stirring, and the contents of the vessel were cooled to −30° C. 36 g Freshly distilled butadiene (667 mM)

having a boiling point of 0° C. was then introduced into the cold liquid in the vessel with continuous stirring. The nitrogen pressure in the vessel was raised to 10 atmospheres in order to reduce the partial butadiene pressure in the gas phase during subsequent heating from −30° to +50° C., and while the elevated temperature was maintained for 24 hours.

The gas under pressure was released thereafter, the vessel was opened, and the liquid reaction product was washed three times with water in a separatory funnel to remove the catalysts. The washed organic phase was subjected to distillation in a vacuum to remove unreacted allyl alcohol.

The residue weighed 34.2 g and was a colorless wax having a melting range of approximately 40° to 50° C., and a boiling point of about 300° to 300° C. (decomp.). When freshly prepared, it was readily soluble in petroleum ether, benzene, toluene, chloroform, and dichloromethane. Its solubility in ether and tetrahydrofuran was good. The waxy product was stable when exposed to light under a nitrogen blanket. It gradually absorbed oxygen when exposed to air and lost its solubility.

Its average molecular weight, as determined by means of a vapor pressure osmometer was 321, and the elementary analysis was consistent with a formula of $OCH-(CH_2)_2-R_n-(CH_2)_3-OH$, wherein R is as defined above and n is 1–10. The yield was 94.8% based on the weight of the diene used.

When the above procedure was repeated, but the reaction time was increased to 30 hours, the same product was obtained in a yield of 99.5%. The yield was not significantly lowered in subsequent runs in which the rhodium catalyst was gradually reduced to 200 mg $Rh(NO_3)_3$, but fell off at lower rhodium amounts. No significant change in average molecular weight was observed in the product from runs with 200 to 1000 mg $Rh(NO_3)_3$ but the molecular weight increased when the amount of $Rh(NO_3)_3$ was reduced to less than 200 mg (0.70 mM).

A sharp reduction in the molecular weight of the product could be brought about by increasing the amount of sodium in the otherwise unchanged procedure outlined above in detail. A ten-fold increase in the amount of sodium reduced the molecular weight to 170, corresponding to a value of n=1 in the general formula of the compound. The yield was simultaneously reduced to slightly less than 20%.

EXAMPLE 2

The procedure of Example 1 was repeated, but lithium was substituted for sodium. 25 mg Lithium (3.6 mM) was combined with 65.1 g allyl alcohol (1.12 M) under a nitrogen blanket in the pressure vessel at 20° C., and 0.987 g $Rh(NO_3)_3$ was stirred in. 35.95 g Butadiene, freshly distilled, was introduced into the vessel whose contents had been cooled to −30° C. The nitrogen pressure was raised to 10 atmospheres, and the vessel was heated to 50° C. It was kept at this temperature for three hours, and the reaction mixture then was worked up as in Example 1.

A closely similar compound having a molecular weight of 1823 was recovered in an amount of 35.47 g (98.7% yield).

The compounds prepared by the methods of Examples 1 and 2 were vulcanized with sulfur in a conventional manner and yielded products closely similar to vulcanized natural rubber. They no longer absorbed oxygen from the air.

EXAMPLE 3

A bath produced according to Example 1 and having an average molecular weight of 330 was converted into an elastomeric polyurethane by the following procedure:

A dispersion of 395 mg sodium (17.2 mM) in 10 ml diethyl ether was mixed with a solution of 1.67 g 1,6-dichloronaphthalene (8.6 mM) in 20 ml ether under a nitrogen blanket. and the mixture was kept at 20° C. for three hours to produce a solution of 1,6-disodium naphthalene. It was combined with stirring at 0° C. with a solution of 2.42 g (7.32 mM) of the aforementioned compound of Example 1 in 10 ml ether. Stirring was continued for one hour. The reaction mixture was diluted with 20 ml petroleum ether and washed four times with 30 ml water. When the solvent was evaporated from the dried, organic phase, a dihydric alcohol of the formula

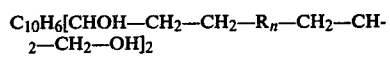

$C_{10}H_6[CHOH-CH_2-CH_2-R_n-CH_2-CH_2-CH_2-OH]_2$ having a molecular weight of 786 was obtained in a yield of almost 100%.

960 Mg of the last mentioned compound (1.22 mM) were dissolved in 5 g toluene and reacted at 80° C. for two hours with 209 mg toluylene-2,4-diisocyanate in the presence of approximately 5 mg bismuth nitrate as a catalyst.

The polyurethane so produced could be vulcanized with sulfur in the usual manner to produce a synthetic rubber having the resiliency of natural rubber similarly vulcanized, but also the greater abrasion resistance and mechanical stability characteristic of elastomeric urethanes. This combination of properties makes the product suitable for use in tires for the wheels of motor vehicles and aircraft.

EXAMPLE 4

The dihydric alcohol prepared in Example 3 was mixed with toluylene-2,4-diisocyanate, and the mixture was extruded through a die opening 1 mm wide and 20 cm long on the wax-coated belt of a conveyor heated to 80° C. Powdered sulfur was dispersed from an air nozzle on the surface of the extrudate and pressed into the soft, heated material by passage between six rollers, causing cross-linking at all double bonds by S—S bridges.

The translucent foils so produced were a better replacement for glass in greenhouse walls and domes employed for distillation of sea water by solar heat than plastic sheets of similar weight employed for the same purpose heretofore. They better resisted the pressure of wind and precipitation because of their resiliency coupled with high ultimate tensile strength. They showed particularly good resistance to propagation of breaks and did not deteriorate under the influence of sunlight.

EXAMPLE 5

In a manner analogous to the procedure of Example 1, 82 mg sodium (3.57 mM) was combined with 65 g allyl alcohol (1.12 M) in a pressure vessel and 1.03 g anhydrous cobalt nitrate (5.63 mM) was added. The cobalt salt was prepared by drying $Co(NO_3)_2.6H_2O$ for two hours at 120° C. in a vacuum. The mixture of catalysts and solvent was cooled to −30° C., and 33.2 g butadiene (0.614 M) was introduced. The contents of the pressure vessel thereafter were held at 60° C. for 40 hours, and the reaction mixture was worked up as in Example 1. The wax-like polymer obtained weighed 6.5 g (19.6% yield) and had an average molecular weight of 381.

EXAMPLE 6

Employing the general procedure of Example 1, a catalyst dispersion was prepared from 79 mg sodium (3.44 mM), 66 g allyl alcohol (1.14 M) and 0.995 g $RhCl_3$ (4.76 mM). 0.691 g Butadiene was polymerized under a nitrogen pressure of 8 atmospheres for 30 hours at 50° C. to produce a 30.8 g polymer (82.4% yield) having an average molecular weight of 269.

When bismuth nitrate was substituted for the rhodium salts in equimolecular amounts, some of the same polymer was formed, but the yield was only about 3%.

The nitrates and chlorides of the other platinum metals (ruthenium, palladium, osmium, iridium, and platinum) were approximately equally effective as the corresponding rhodium compounds. The latter, however, are preferred at this time since they are readily available, and the recovery of the rhodium values from the spent catalyst on a commercial scale is a well developed art.

Iron and nickel nitrate produce about the same yields as cobalt nitrate, and no significant change in yield is achieved by the use of the chlorides instead of the nitrate employed in Example 5.

When isoprene, 2,3-dimethylbutadiene, or chloroprene were substituted in the procedures of the several Examples, closely analogous results were achieved. More specifically, a waxy product capable of reacting with disodium naphthalene and of further reacting with toluylene-diisocyanate to produce a vulcanizable elastomer was produced when each of the three butadiene homologs and analogs was substituted in the process of Example 1.

I claim:
1. A compound of the formula

$$OCH-(CH_2)_2-R_n-(CH_2)_3-OH$$

wherein R is a radical of the formula $C_4H_{6-m}X_m$ having a straight chain of four carbon atoms,
X is hydrogen, methyl, or chlorine.
m is 1 or 2 when X is methyl or hydrogen,
m is 1 when X is chlorine, and
n is a number between 1 and 60.

2. A compound as set forth in claim 1, wherein n is greater than one.
3. A compound as set forth in claim 2, wherein R is $-C_4H_6-$.
4. A compound as set forth in claim 3, wherein R is $-CH_2-CH=CH-CH_2-$.
5. A compound as set forth in claim 3, wherein R is $$-CH_2-\underset{|}{CH}-CH=CH_2- \ .$$

6. A compound as set forth in claim 2, wherein R is $-C_5H_8-$.
7. A compound as set forth in claim 2, wherein R is $-C_4H_5Cl-$.
8. A compound as set forth in claim 2, wherein R is $-C_6H_{10}-$.
9. A compound as set forth in claim 1, wherein n is 1 to 10.

* * * * *